(12) United States Patent
Ebrahim et al.

(10) Patent No.: US 9,839,388 B2
(45) Date of Patent: Dec. 12, 2017

(54) PERSONALITY ASSESSMENT AND TREATMENT DETERMINATION SYSTEM

(71) Applicants: Mahdi S. H. S. A. Al-Sayed Ebrahim, Safat (KW); Abrar H. A. Al-Bahrani, Safat (KW)

(72) Inventors: Mahdi S. H. S. A. Al-Sayed Ebrahim, Safat (KW); Abrar H. A. Al-Bahrani, Safat (KW)

( * ) Notice: Subject to any disclaimer, the term of this patent is extended or adjusted under 35 U.S.C. 154(b) by 0 days.

(21) Appl. No.: 15/226,776

(22) Filed: Aug. 2, 2016

(65) Prior Publication Data

US 2017/0258385 A1  Sep. 14, 2017

Related U.S. Application Data

(60) Provisional application No. 62/307,496, filed on Mar. 13, 2016.

(51) Int. Cl.
*G09B 19/00* (2006.01)
*A61B 5/16* (2006.01)
(Continued)

(52) U.S. Cl.
CPC ............ *A61B 5/165* (2013.01); *A61B 5/0077* (2013.01); *A61B 5/1176* (2013.01); *A61B 5/15* (2013.01);
(Continued)

(58) Field of Classification Search
CPC ......... A61B 5/165; A61B 5/15; A61B 5/7282; A61B 5/742; A61B 5/1176; A61B 10/007;
(Continued)

(56) References Cited

U.S. PATENT DOCUMENTS 5,692,501 A   12/1997  Minturn
6,494,830 B1 *  12/2002  Wessel ............... A61B 5/04325
                                                          273/459

(Continued)

FOREIGN PATENT DOCUMENTS

TW      201244695 A1   11/2012
WO   WO 2009/126039 A1   10/2009

OTHER PUBLICATIONS

Psychology Topics > Personality. http://www.alleydog.com/topics/personality.php (Lasted Accessed on Jul. 13, 2015) pp. 1-15.

(Continued)

*Primary Examiner* — Michael Grant
(74) *Attorney, Agent, or Firm* — Richard C. Litman

(57) ABSTRACT

The personality assessment and treatment determination system includes a facial recognition device for imaging a patient's face and receiving demographic and personality information from the patient, and a micro-lab device positioned in communication with the facial recognition device. The micro-lab device includes a body having at least one slot configured for receiving a slide holding the patient's bodily fluid, a scanner for analyzing the patient's bodily fluid, and a selector switch for selecting the bodily fluid to be analyzed. The information from the facial recognition device, each of the plurality of questionnaires, and from the micro-lab device is combined to determine the patient's psychological disorder and a treatment for the patient's psychological disorder.

6 Claims, 12 Drawing Sheets

(51) Int. Cl.
   *A61B 5/1171* (2016.01)
   *A61B 5/00* (2006.01)
   *A61B 5/15* (2006.01)
   *A61B 10/00* (2006.01)

(52) U.S. Cl.
   CPC ............ *A61B 5/7282* (2013.01); *A61B 5/742* (2013.01); *A61B 10/007* (2013.01); *A61B 10/0051* (2013.01); *A61B 2560/0431* (2013.01)

(58) Field of Classification Search
   CPC .............. A61B 10/0051; A61B 5/0077; A61B 2560/0431
   USPC ...................... 434/236; 436/55, 164; 422/400
   See application file for complete search history.

(56) References Cited

U.S. PATENT DOCUMENTS

| | | | |
|---|---|---|---|
| 7,231,240 | B2 | 6/2007 | Eda et al. |
| 8,918,162 | B2 | 12/2014 | Prokoski |
| 2002/0059030 | A1* | 5/2002 | Otworth ................ A61B 5/411 702/19 |
| 2002/0118355 | A1* | 8/2002 | Worthington .... G01N 35/00069 356/72 |
| 2004/0096363 | A1* | 5/2004 | Porter ................ G01N 21/8483 422/68.1 |
| 2005/0043894 | A1* | 2/2005 | Fernandez ........... A61B 5/0215 702/19 |
| 2008/0126123 | A1 | 5/2008 | Duckert |
| 2008/0154894 | A1 | 6/2008 | Chen et al. |
| 2008/0162352 | A1 | 7/2008 | Gizewski |
| 2010/0010371 | A1* | 1/2010 | Zayfert ................... A61B 5/16 600/558 |
| 2010/0292545 | A1* | 11/2010 | Berka .................... A61B 5/048 600/301 |
| 2011/0165688 | A1* | 7/2011 | Dupoteau ............ A61B 5/1172 436/55 |
| 2011/0294099 | A1 | 12/2011 | Brady |
| 2013/0281798 | A1* | 10/2013 | Rau ...................... A61B 5/4884 600/301 |
| 2014/0296089 | A1* | 10/2014 | Holmes ................ G01N 35/026 506/9 |
| 2014/0330576 | A1* | 11/2014 | Bauer ................. G06F 19/3418 705/2 |
| 2015/0313524 | A1* | 11/2015 | Matsumoto ........ A61B 10/0064 600/573 |
| 2016/0080548 | A1* | 3/2016 | Erickson ........... H04M 1/72527 455/556.1 |
| 2016/0249847 | A1* | 9/2016 | Kennedy ............. A61B 5/4266 600/307 |
| 2016/0324506 | A1* | 11/2016 | Tariyal ............... A61B 10/0045 |
| 2016/0350801 | A1* | 12/2016 | Vincent .............. G06Q 30/0251 |
| 2017/0039336 | A1* | 2/2017 | Bitran ................. A61B 5/6801 |

OTHER PUBLICATIONS

Ellis Questionaire http://www.google.com/url?sa=t&rct=j&q=&esrc=s&source=web&cd=2&cad=rja&uact=8&ved=OCCkQFjABahUKEwjp9pGlqtjGAhWKGD4KHWF3A8w&url=http%3A%2F%2Fmisterwoodynotebook.us%2Fsportspsych%2Fellisquestionnaire.doc&ei=28yjVamdL4qx-AHh7o3gDA&usg=AFQjCNHNdLwustVIVCMpijMhuEFDu7rFhA&bvm=bv.97653015,d.cWw (Last Accessed on Jul. 13, 2015) pp. 1-2.

Guimon, Jose, et al. "*Shame, sensitivity to punishment and psychiatric disorders.*" The European Journal of Psychiatry 21.2 (2007): 124-133.

* cited by examiner

PERSONALITY ASSESSMENT AND TREATMENT DETERMINATION SYSTEM

CROSS-REFERENCE TO RELATED APPLICATIONS

This application claims the benefit of U.S. Provisional Patent Application Ser. No. 62/307,496, filed on Mar. 13, 2016.

BACKGROUND OF THE INVENTION

1. Field of the Invention

The present invention relates to psychological assessment system and method, and particularly to a system and method for developing a psychological treatment strategy based on a patient's facial recognition, chemical analysis, and response to questionnaires.

2. Description of the Related Art

The connection between a person's mind and physical health has been under investigation for years. For example, over the past 40 years research has shown that psychological factors can play a major role in illnesses, such as heart disease, and that certain mind-body techniques can aid in the treatment of such illnesses. Further, it has been determined that although behavioral disorders, such as autism, have a biological basis, such disorders can be treated through the mind-body techniques.

Research aimed at determining the connection between a person's mind and physical health also seems to indicate that personality traits and behavioral disorders, such as anxiety, depression, frustration, and shame, can also adversely impact a person's health. Regardless of the amount of research that has been done in this area, there remain certain challenges in terms of accurately acquiring the necessary data to not only identify a person's personality traits, but also to treat the associated psychological disorder and, thereby, treat the corresponding illness.

Thus, a method of developing a psychological treatment strategy solving the aforementioned problems is desired.

SUMMARY OF THE INVENTION

The personality assessment and treatment determination system includes a facial recognition device for imaging a patient's face and receiving demographic and personality information from the patient, and a micro-lab device positioned in communicating relation with the facial recognition device. The micro-lab device includes a body having at least one slot configured for receiving the patient's bodily fluid, a scanner for analyzing the patient's bodily fluid, and a selector switch for selecting the bodily fluid to be analyzed. The information from the facial recognition device, each of the plurality of questionnaires, and from the micro-lab device is combined to determine the patient's psychological disorder and a treatment for the patient's psychological disorder.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
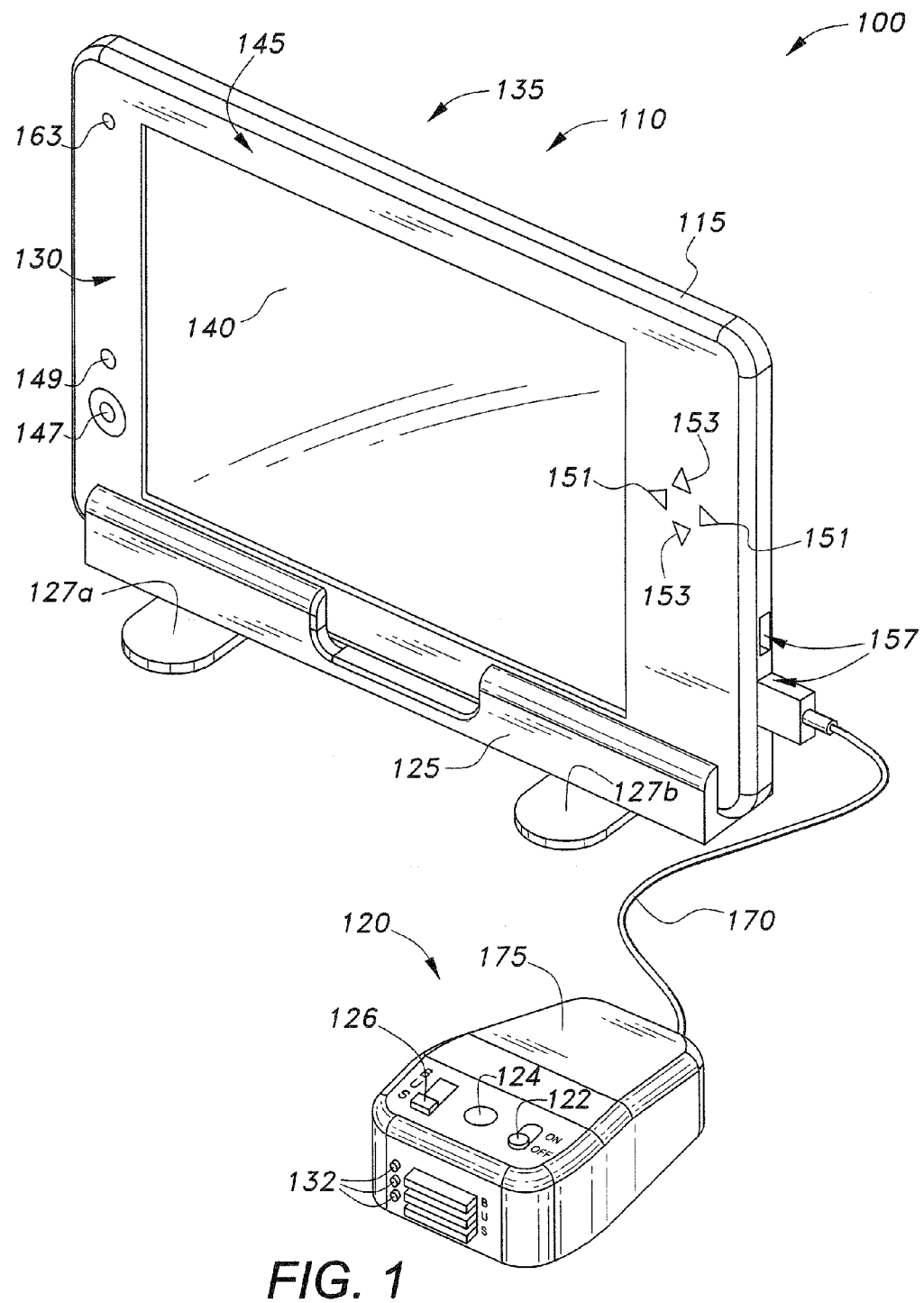
FIG. 1 is an environmental view of a personality assessment and treatment determination system, according to the present invention.
Figure 2:
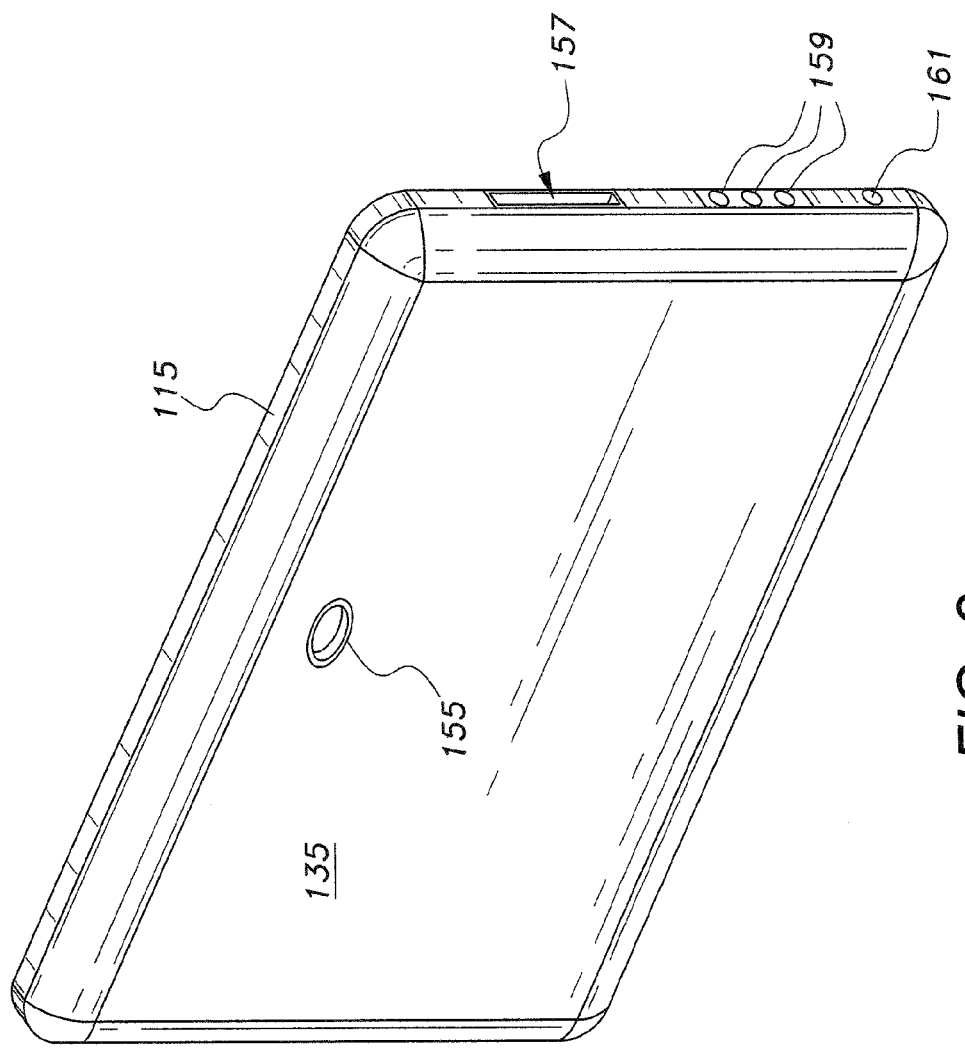
FIG. 2 is a rear, perspective view of a facial recognition device utilized by the personality assessment and treatment determination system, according to the present invention.
Figure 3:
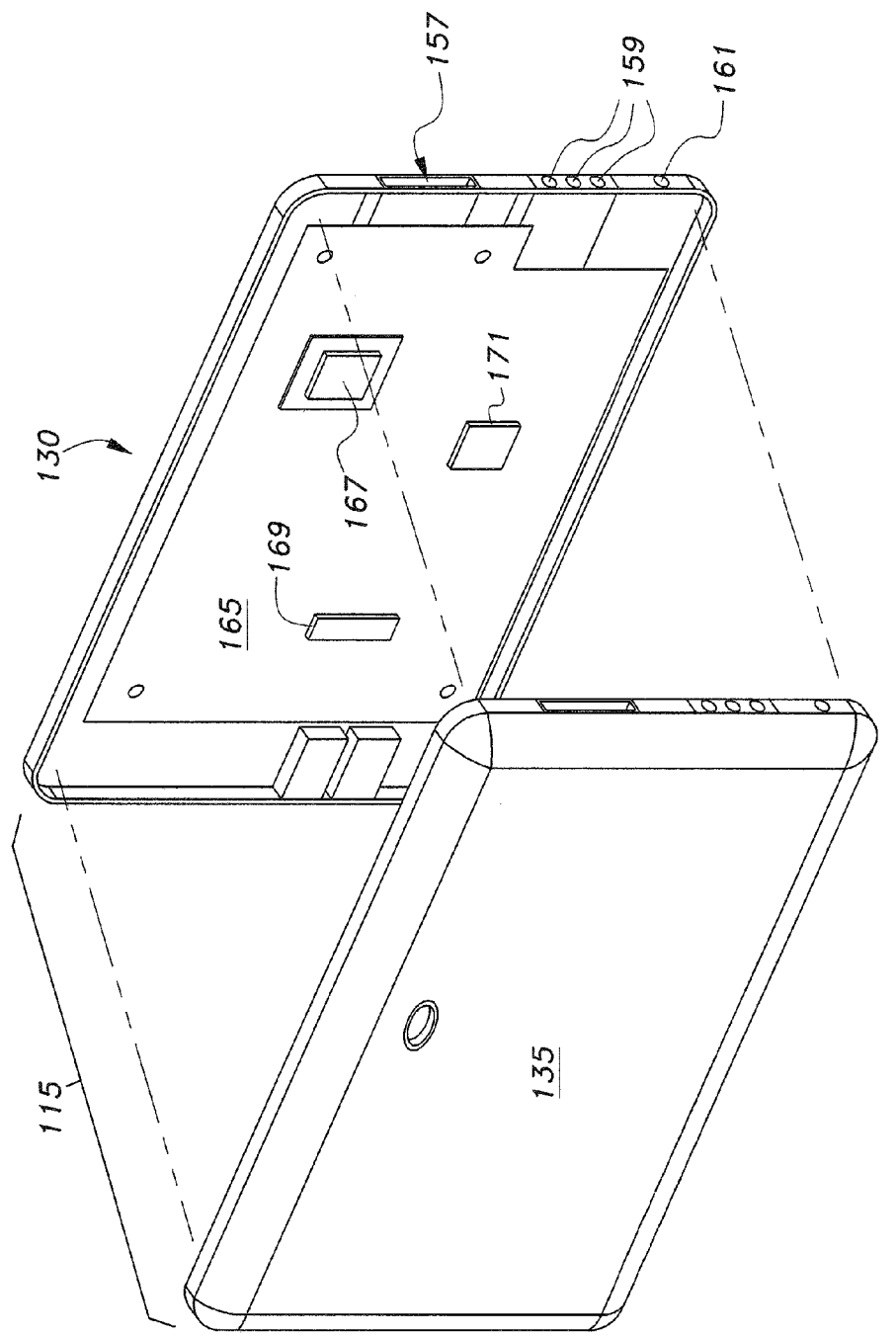
FIG. 3 illustrates the components of the facial recognition device utilized by the personality assessment and treatment determination system, according to the present invention.

Referring to FIGS. 1 through 10, a personality assessment and treatment determination system 100 is generally illustrated. The system 100 comprises a facial recognition device 110 and a micro-lab device 120 in communication with the facial recognition device 110. The facial recognition device 110 is configured for imaging a patient's face. The facial recognition device 110 includes a display or screen 140 for presenting questions to a patient regarding the patient's demographic information, such as gender, age, religion, and personality traits, such as anxiety, depression, gloominess/frustration, and shyness. The micro-lab device 120 is configured to receive and analyze biological samples from a patient. Any suitable software can be installed on the system 100 to combine the results from the facial recognition device 110, the results from the micro-lab device 120, as well as the information from each questionnaire to determine the patient's personality disorder(s) and determine a corresponding treatment for the patient's emotional disorders.

The facial recognition device 110 can include any type of facial recognition device already known in art that can analyze a patient's facial features from a digital image or from a video frame, such as from a video source (not shown), and compare the patient's facial features to those stored on a facial recognition database, such as by comparing the whole facial image or cropping the image and comparing specific portions extracted from the facial image. Patch matching can be applied to find similar features located within a space for categorization. Further, by selecting specific regions of the patient's face to compare, the time needed for computation can be reduced.

The facial recognition device 110 includes a monitor 115 having a front side 130 facing toward the patient and a back side 135 facing away from the patient. The front side 130 includes a screen 140, such as a touch screen to input the demographic information and the questionnaire responses. The screen 140 can be any suitable type of screen 140, such as a light emitting diode (LED) or liquid crystal display (LCD) for displaying results. The patient can also use a keyboard (not shown) to enter his/her questionnaire responses into the system 100. The monitor 115 includes a cover 145 configured for protecting the screen 140 and a plurality of buttons, such as an on/off button 147, a restart button 149, search buttons 151, and download buttons 153.

The back side 135 of the monitor 115 includes a camera 155 configured for imaging the patient's face so as to conduct a facial analysis. A basic facial analysis can aid in determining a patient's skin condition. For example, if during the facial recognition process blue and white markings appear on a screen 140, the patient can have normal and healthy skin. If, on the other hand, light violet hues appear on the screen, the patient can have dehydrated skin. Other types of skin conditions that can be detected include the identification of dead skin cells, hydrated skin, and oily skin. The monitor 115 also includes at least one USB port 157, audio ports 159 that can be used for a soundcard (not shown), a microphone input 161 that can be used for sound recording, and a speaker 163.

The facial recognition device 110 also includes a motherboard 165 having a controller/processor 167 and a memory 169 such as to store data and information, as well as program(s) or instructions for implementing the system 100. The controller/processor 167 can be any suitable type of computer processor, such as a microprocessor or an ASIC, and the calculations, determinations, data transmission or data reception, sending or receiving of control signals or commands processed or controlled by the controller/processor 167 can be displayed on the screen 140 of the monitor 115. The memory 169 can be any suitable type of computer readable and programmable memory, such as non-transitory computer readable media, random access memory (RAM) or read only memory (ROM), for example. The system facial recognition device 110 can also be powered by a system power source 171, such as a battery, for example, as can power operation of the monitor 115, as well as the micro-lab device 120.

Figure 4A:
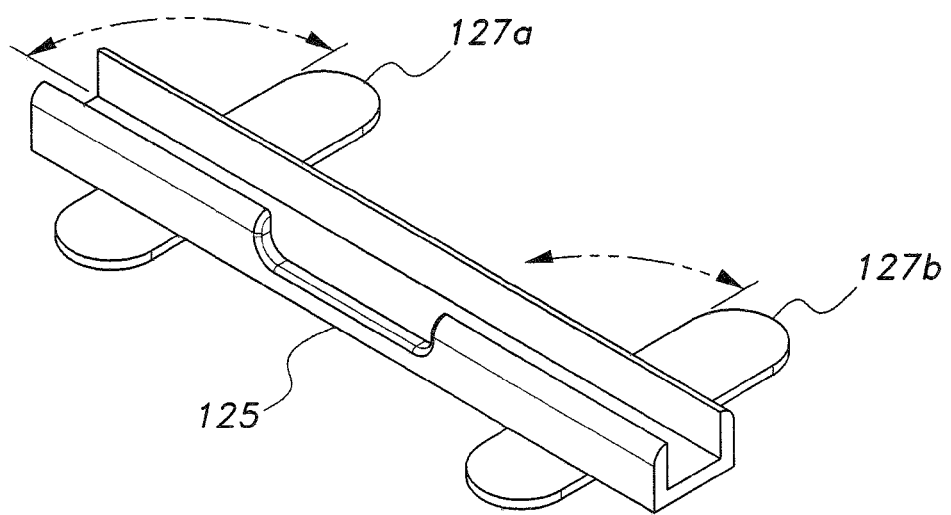
FIG. 4A illustrates a holder configured to support the facial recognition device, wherein each of the rotating legs are rotated outward so as to support the facial recognition device, according to the present invention.
Figure 4B:
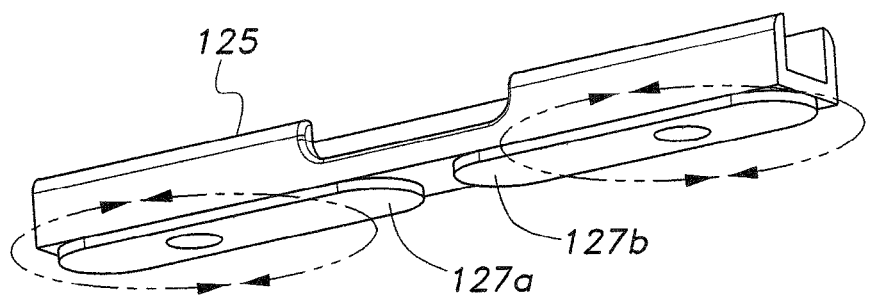
FIG. 4B illustrates a holder configured to support the facial recognition device, wherein each of the rotating legs are rotated inward, according to the present invention.
Figure 5:
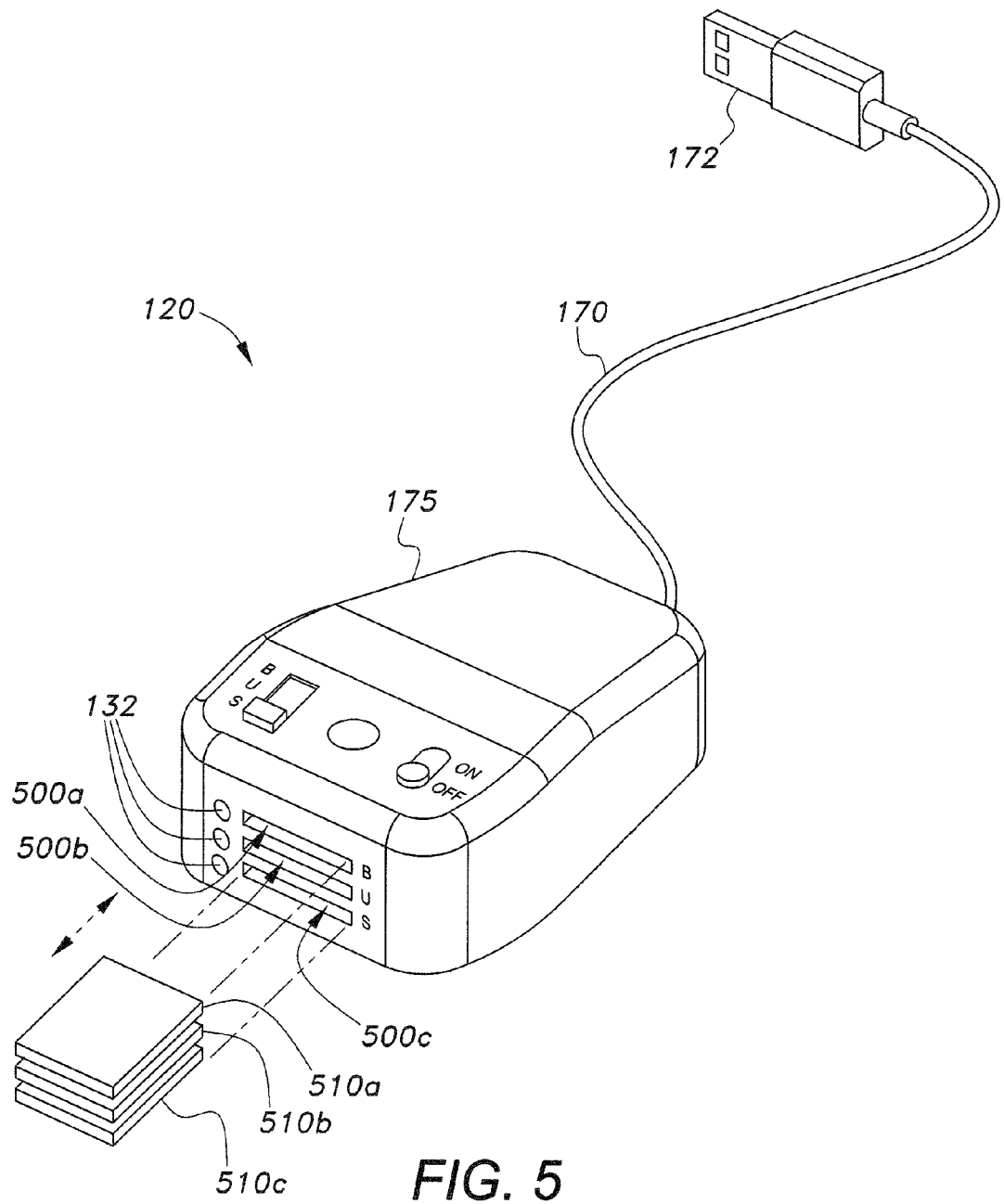
FIG. 5 illustrates a micro-lab device utilized by the personality assessment and treatment determination system, according to the present invention.
Figure 6:
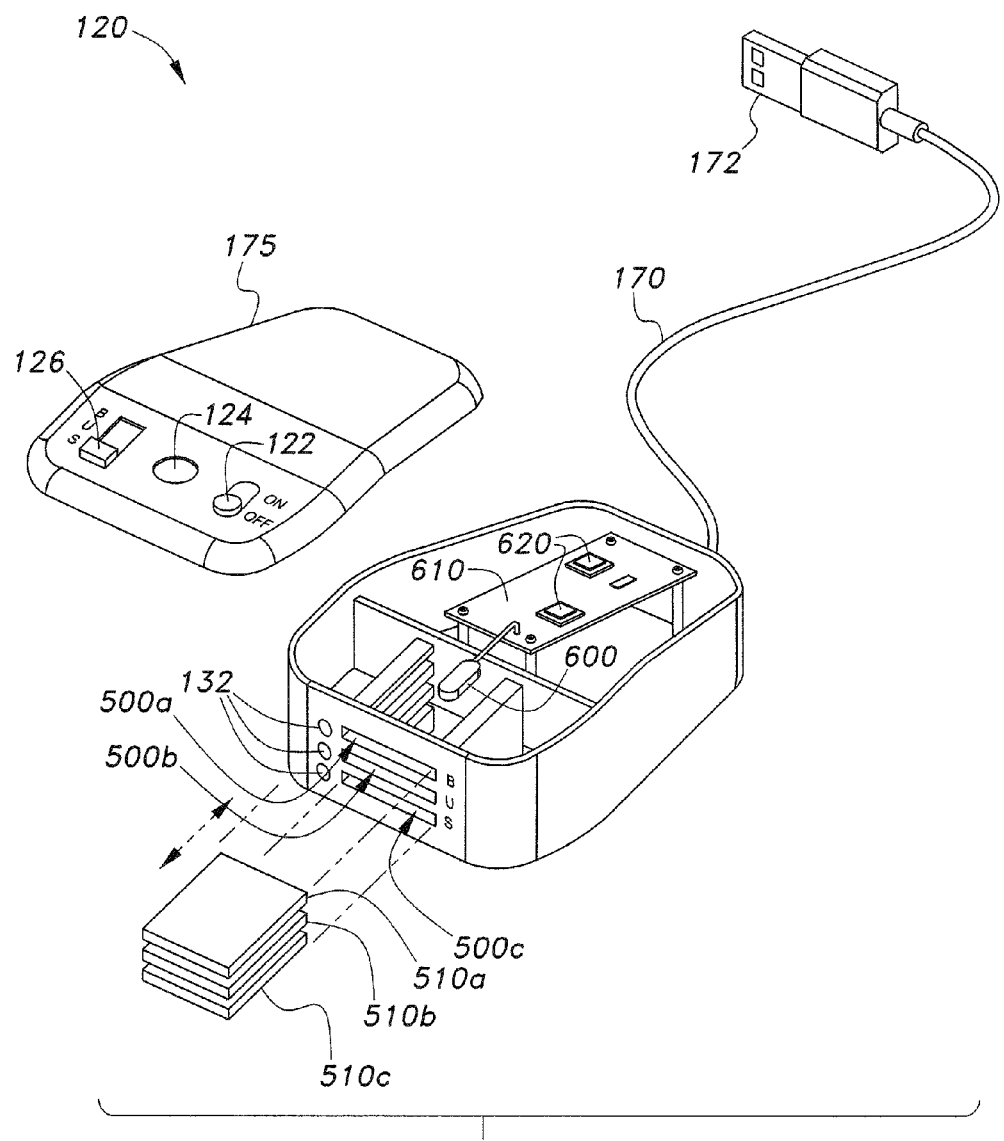
FIG. 6 illustrates the components of the micro-lab device utilized by the personality assessment and treatment determination system, according to the present invention.
Figure 7:
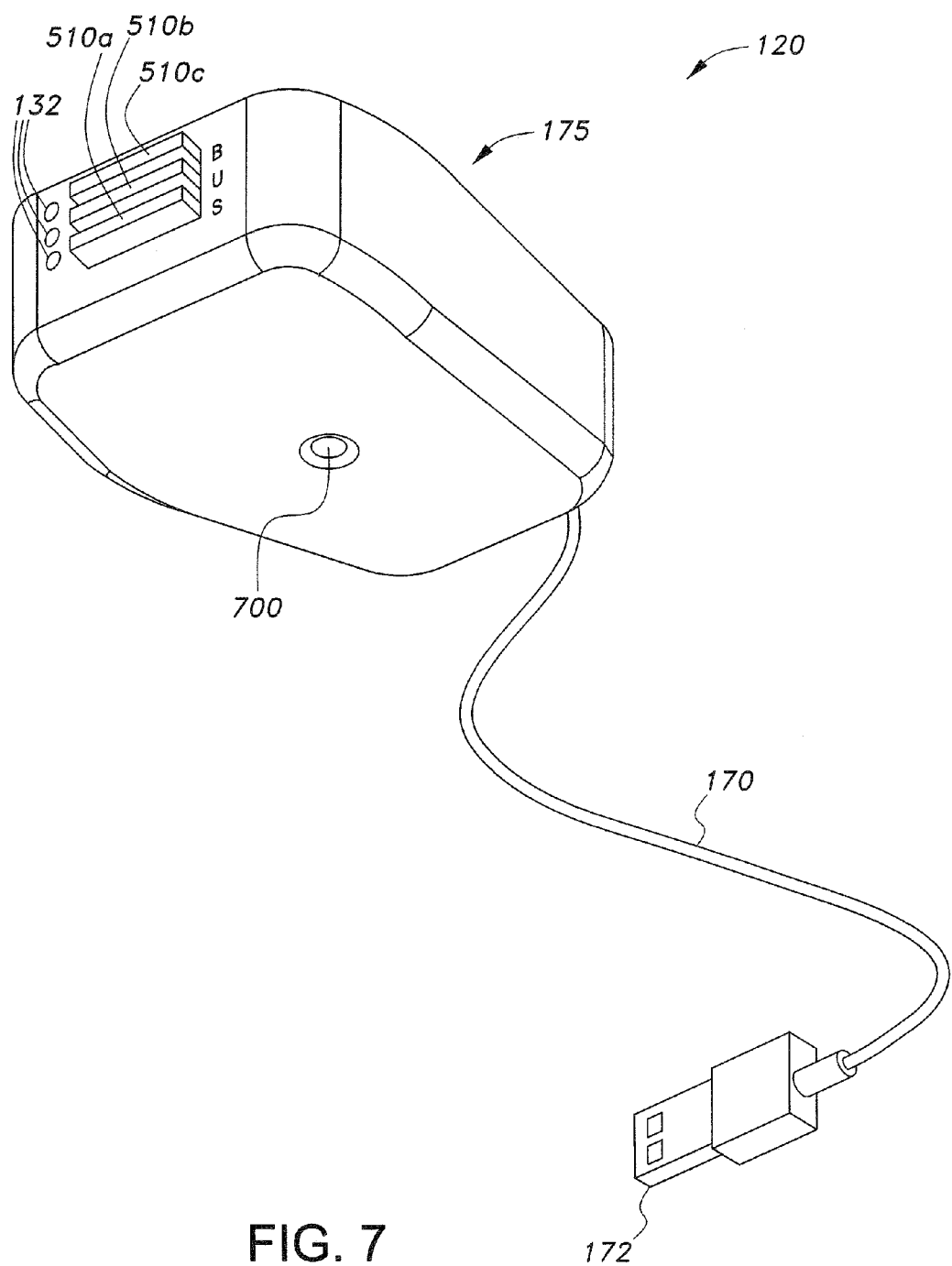
FIG. 7 is a bottom, perspective view of the micro-lab device utilized by the personality assessment and treatment determination system, according to the present invention.

The facial recognition device 110 can be supported by a holder 125 having a plurality of rotating support legs, such as a first rotating support leg 127a and a second rotating leg 127b. The first rotating support leg 127a and the second rotating support leg 127b can rotate in any direction, such in an outward (e.g. clockwise) direction to support the holder 125 and in an inward (e.g. counterclockwise) direction to lock the rotating support legs 127a-127b underneath the holder 125, as illustrated in FIGS. 4A and 4B, such as to make it easier to store and/or transport.

The micro-lab device 120 is configured for analyzing the chemical compositions of a variety of a patient's bodily fluids, such as blood B, urine U, and saliva S, to determine the patient's body chemistry, such as the levels of Acetylcholine, Serotonin, Adrenaline, pH, and Glucose and whether a patient is susceptible to a certain disorder, such as anxiety, gloominess, depression, and shyness.

The micro-lab device 120 is in communicating relation with the facial recognition device 110, such as via a cable 170 having a USB connector 172 or via a wireless connection, such as Bluetooth®. The micro-lab device 120 includes a body 175 having a plurality of slots, such as a first slot 500a, a second slot 500b, and a third slot 500c, each slot 500a-500c configured for receiving a slide, such as a first slide 510a, a second slide 510b, and a third slide 510c, a scanner 600 configured for scanning each slide 510a-510c, and a selector switch 126 configured for selecting the slide 510a-510c that is to be analyzed.

In use, for example, the sample of the patient's blood B can be deposited on the first slide 510a and inserted into the first slot 500a, the sample of the patient's urine U can be deposited on the second slide 510b and inserted into the second slot 500b, and the sample of the patient's saliva S can be deposited on the third slide 510c and inserted into the third slot 500c. Alternatively, the body 175 of the micro-lab device 120 can include a single slot and a selector switch 126, which can be adjusted by a user to indicate what kind of biological sample is to be processed.

The scanner 600 can be any suitable type of scanner, such as a substance recognition scanner. The scanner 600 is positioned above the slides 510a-510c, to scan each type of bodily fluid contained on each slide 510a-510c. Although not shown, it is to be understood that the micro-lab device 120 can include a plurality of scanners (desirably three scanners) in a vertical arrangement, with each scanner positioned above a respective one of the slides 510a-510c, to prevent or minimize the risk of contamination of the bodily fluids being examined and maintain the accuracy of the results. Scanners that can be used in the micro-lab device 120 include a saliva scanner configured to determine a patient's pH level and a light based scanner configured for determining acetylcholine levels. A pattern recognition scanner or a level recognition scanner can also be used, such as for determining whether a pattern exists among the chemical compositions of the bodily fluids, as well as whether any color variation and/or any tune variation among the bodily fluids exists. The scanner 600 may be adjusted, such as adjusted automatically, to obtain the best resolution for each of the samples of bodily fluids on each corresponding slide 510a-510c. For example, the distance between the scanner 600 and each slide 510a-510c can be altered so as to obtain a clearer image. The results as determined by the scan of each bodily fluid by the scanner 600 can then be displayed on the screen 140 of the facial recognition device 110.

A simple blood test can serve as a diagnosis tool for stress and depression. For example, the blood test may reveal if the patient is unable to handle stress and whether a certain medical treatment would help. Such an exam could be helpful for soldiers returning from war zones or for people having been subjected to severe stress, such as after terrorist attacks or natural disasters.

Acetylcholine (ACh) is an organic chemical that is present in the brain and body of many types of animals, including humans, as a neurotransmitter (i.e. a chemical released by the nerve cells to send signals to other cells). Over the years research has shown that when the body feels stress, such as when a child jumps in front of a moving car, the level of ACh in the synapsis increases. For the body to return to normal ACh levels a special enzyme called Acetylcholinesterase (AChE), which breaks down ACh, increases so as to bring the ACh levels back to normal levels. After the stress event disappears, the levels of ACh and AChE tend to decrease. However, people who suffer from anxiety disorders tend to maintain high levels of ACh and AChE. As such, a blood test can detect an increase in the ACh and the corresponding AChE levels so as to determine a patient's ability to deal with stress and whether they have an anxiety disorder.

The micro-lab device 120 further includes an on/off switch 122 and a motherboard 610 positioned in communication with the scanner 600. The motherboard 610 is configured to avoid data loss between the micro-lab device 120 and the facial recognition device 110. The motherboard 610 of the micro-lab device 120 includes a first processor unit 615 configured for processing the scanned specimen and transmitting the data to a second processor unit 620 configured for communicating with a database (not shown) containing chemistry reference material so that the chemical composition of the patient's blood B, urine U, and saliva S (or whichever bodily fluids are being analyzed) can be determined.

An indicator light 124 positioned in the body 175 of the micro-lab device 120 is configured for indicating the completion of the scanning process. The body 175 of the micro-lab device 120 also includes a plurality of ejection buttons 132, configured for ejecting a corresponding slide 510a-510c, and an LED assembly 700 configured for movement detection such that the micro-lab device 120 can also be used as a mouse and move a cursor (not shown) on the screen 140.

Figure 8A:
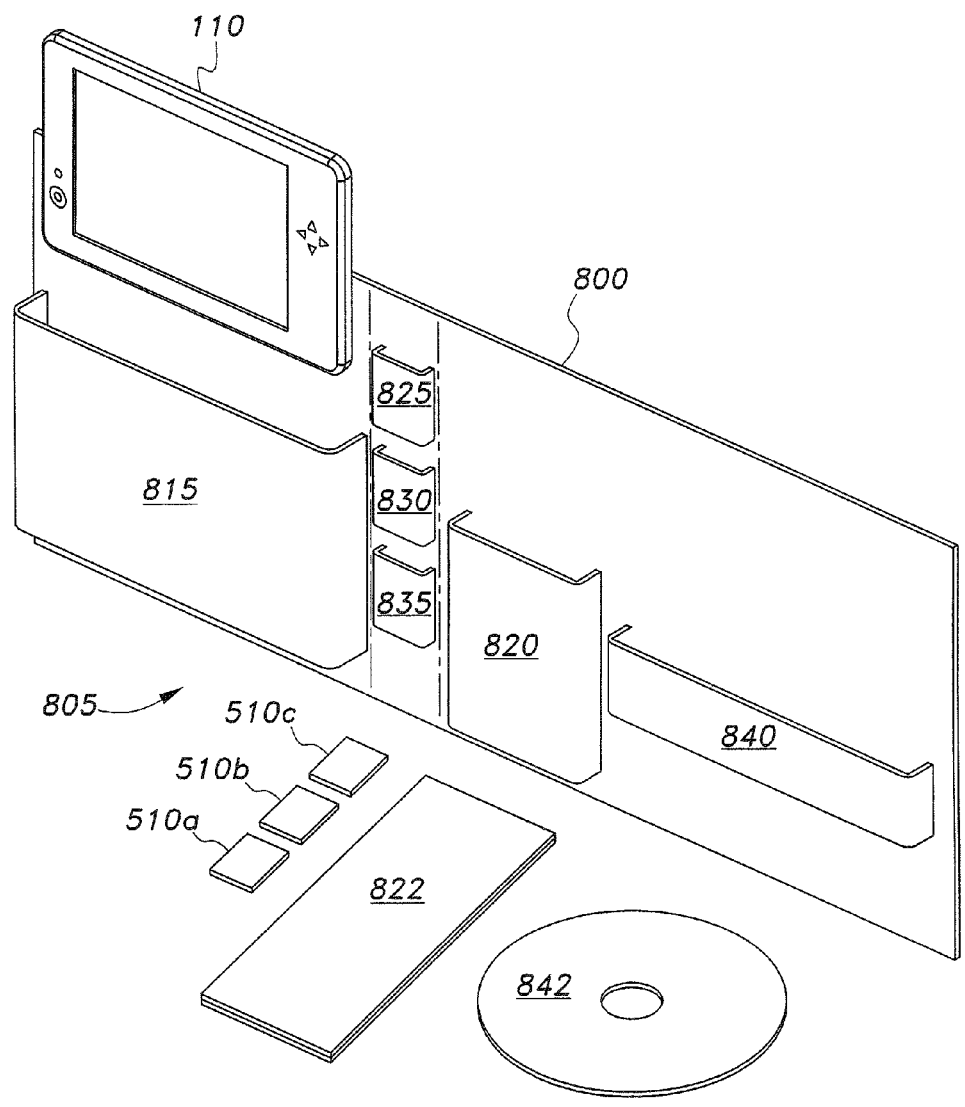
FIG. 8A illustrates an interior portion of a case having a plurality of compartments configured for carrying components of the personality assessment and treatment determination system, according to the present invention.
Figure 8B:
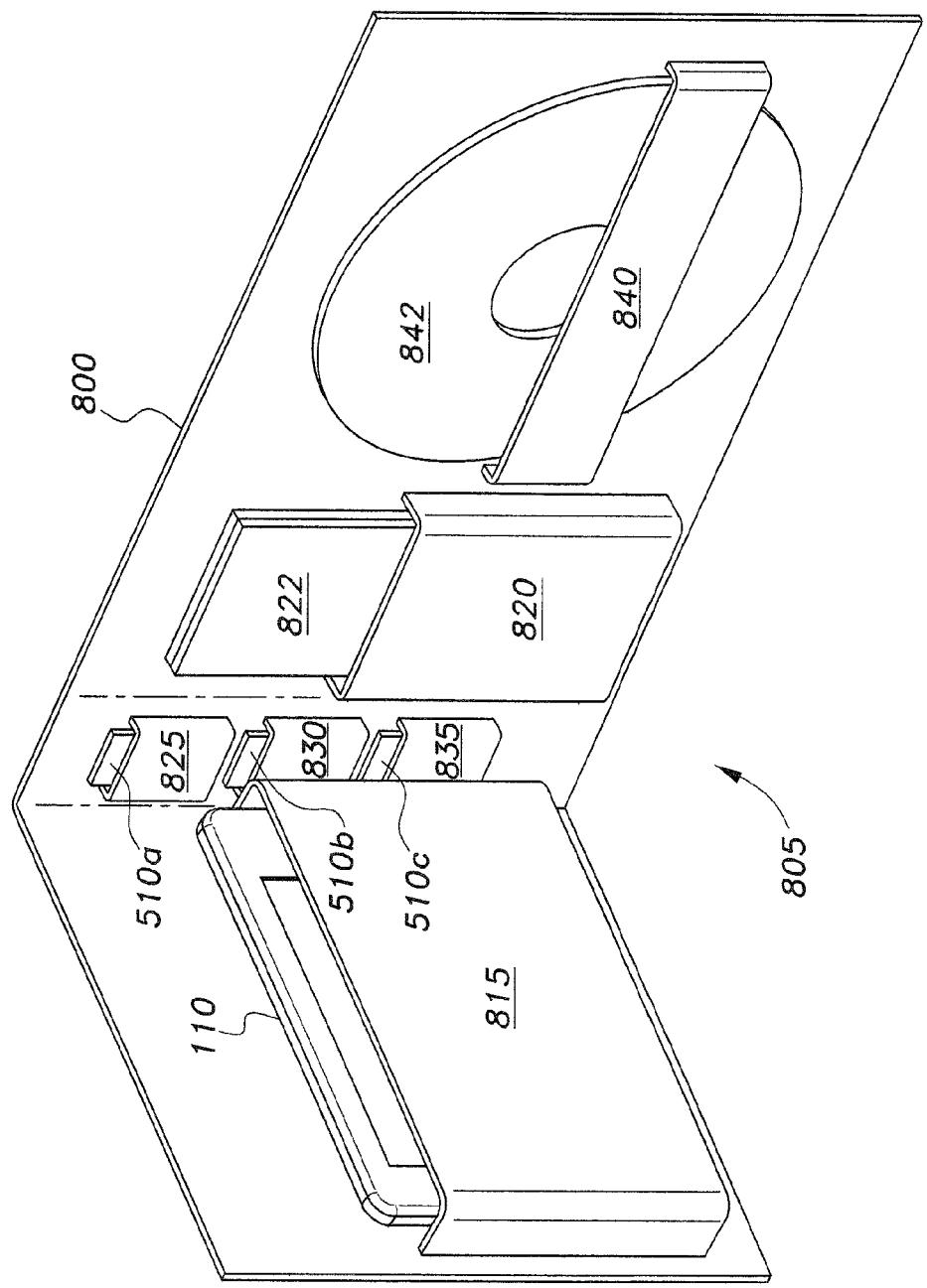
FIG. 8B illustrates components of the personality assessment and treatment determination system inserted into the interior portion of the case, according to the present invention.

Referring to FIGS. 8A and 8B, both the facial recognition device 110 and the micro-lab device 120 can be stored and transported in a case 800, such as a portfolio case, having an interior portion 805 and an exterior portion 810. The interior portion 805 of the case 800 includes a plurality of compartments, such as a first compartment 815 for storing the facial recognition device 110, a second compartment 820 for storing a manual 822, a third compartment 825 for storing the first slide 510a, a fourth compartment 830 for storing the second slide 510b, a fifth compartment 835 for storing the third slide 510c, as well as a sixth compartment 840 for storing a disk 842, or other such type(s) of computer readable media with preprogrammed software instructions. Examples of the disks include a DVD (Digital Versatile Disc), a DVD-RAM, a CD-ROM (Compact Disc-Read Only Memory), and a CD-R (Recordable)/RW. FIG. 8B illustrates the interior portion 805 of the case 800 carrying the corresponding equipment, described above.

Figure 8C:
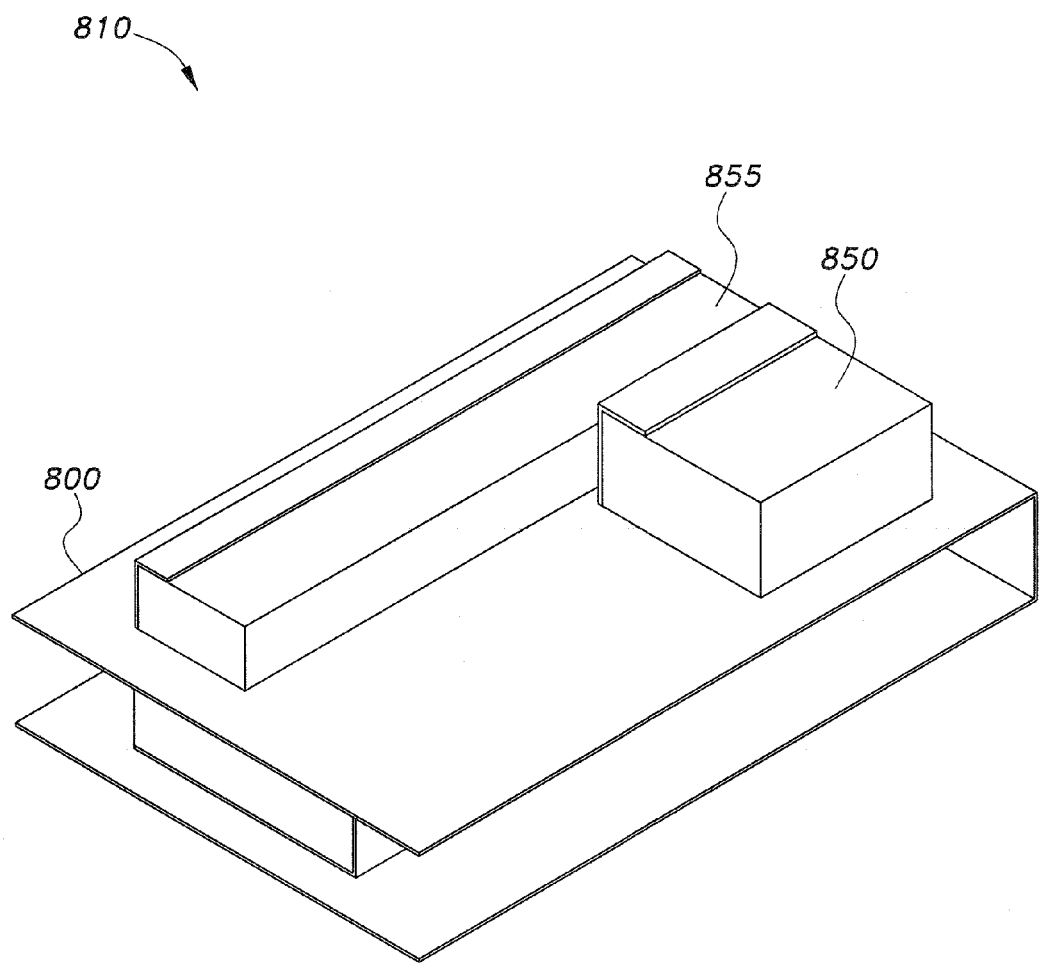
FIG. 8C illustrates an exterior portion of the case having a plurality of compartments configured for carrying components of the personality assessment and treatment determination system, according to the present invention.

Referring to FIG. 8C, the exterior portion 810, on the other hand, also includes a plurality of compartments, such as a first compartment 850 for storing the micro-lab device 120 and a second compartment 855 for storing writing utensils, such as pens and pencils.

The questionnaires can include questions to reveal a patient's particular emotional state, such as anxiety, frustration, depression, and shyness. As such, each questionnaire can aid in diagnosing the patient's psychological and physiological conditions. It is to be understood that the questions can be altered so as to examine a variety of other emotional states. Each questionnaire includes a plurality of questions, such as ten (10) questions, each question having at least three responses, such as "Do Not", "Sometimes", and "Yes", each response having a corresponding value, such as "1" "2", or "3". A person, such as a psychiatrist or psychologist, administering the questionnaire(s) can sum up the total score from each questionnaire so as to achieve a total score and, in turn, the patient's personality traits, as well as the intensity of the respective personality trait(s). For example, a total score of between 10 and 15 indicates normal, a total score of between 16 and 20 indicates a simple state disorder, a total score of between 21 and 25 indicates a moderate state disorder, and a total score of between 26 and 30 indicates a severe state disorder.

Figure 9:
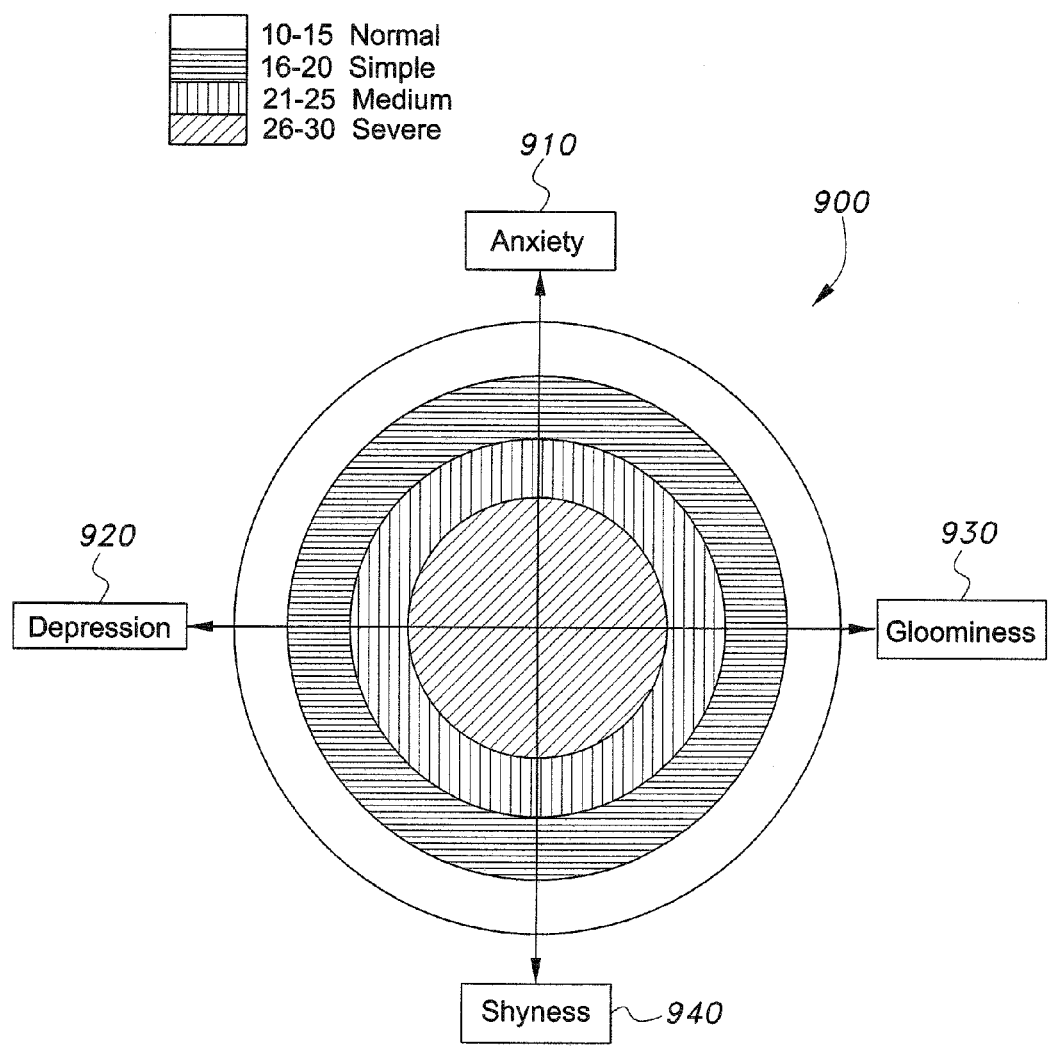
FIG. 9 illustrates a chart for plotting the results of questionnaires directed to anxiety, depression, gloominess, and shyness, according to the present invention.

Referring to FIG. 9, once the patient completes each questionnaire, his/her scores can be inputted into a table, such as an Excel® table, having a plurality of columns, such that the patient answering the questionnaire has a total score for Anxiety 910, a total score of Depression 920, a total score for Gloominess 930, and a total score for Shyness 940. Each total score for each condition can then be plotted on a graph 900.

Figure 10:
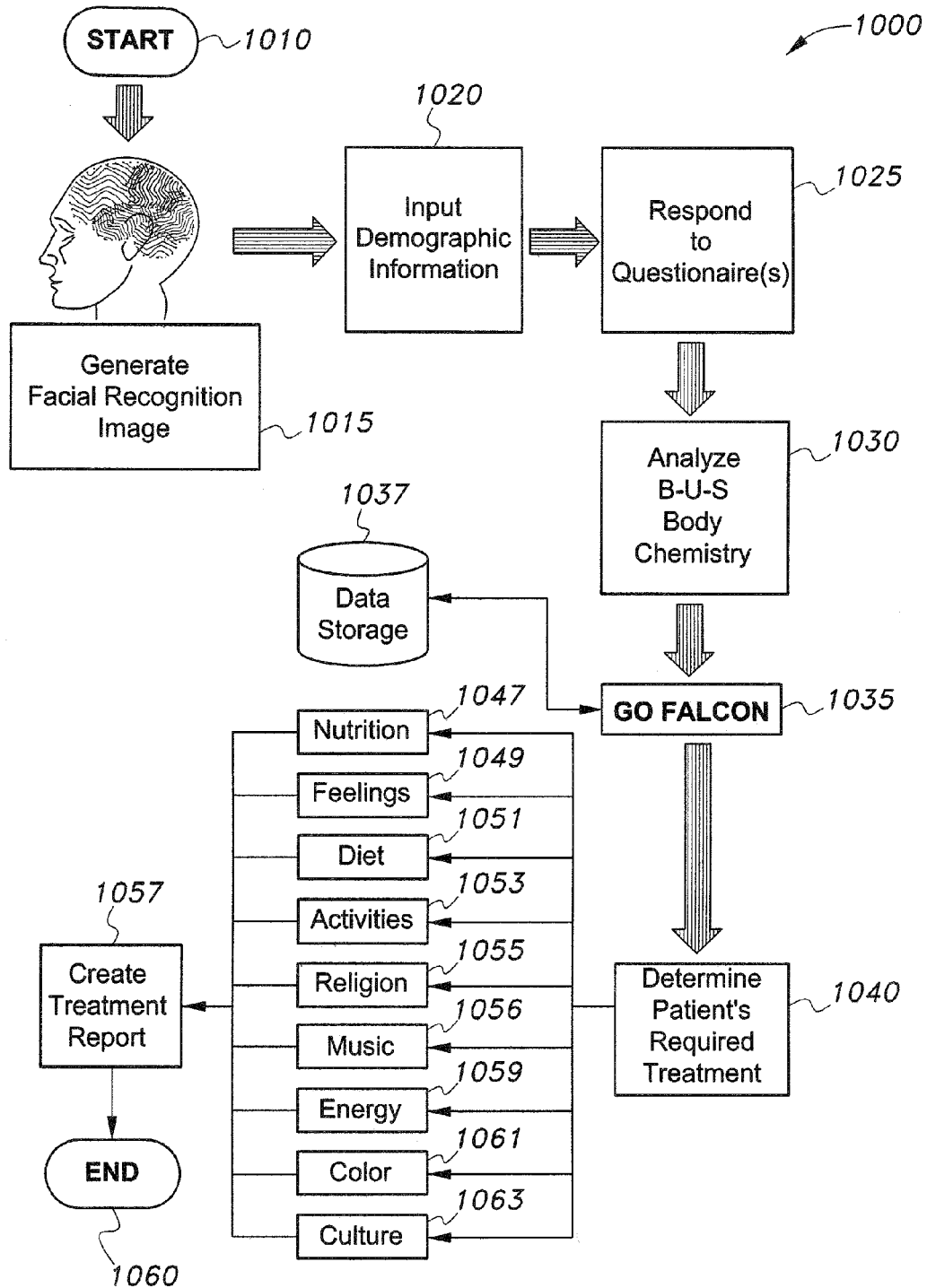
FIG. 10 illustrates a process for assessing a patient's personality and determining a treatment, according to the present invention.

Referring to FIG. 10 there is illustrated a process flow 1000 that illustrates and implements a process and method for determining the patient's personality disorder, such as anxiety, depression, shyness, and/or gloominess, the intensity of such disorder(s), and determining a proper treatment. To start (Step 1010) the process 1000, a physician, for example, first generates an image of the patient's face using the camera 155 on the back side 135 of the facial recognition device 110 (Step 1015). Once the facial analysis has been completed and appears on the screen 140 of the monitor 115, the patient's facial features are compared with those maintained on the facial recognition database to determine the patient's personality traits. The patient's facial expression can be used to determine if s/he is happy, sad, indifferent, angry, disgusted, fearful, or surprised.

After the facial recognition is complete (Step 1015), the patient then, using the touch screen 140 or the keyboard (not shown), inputs the necessary demographic information, such as such as gender, age, religion, and qualifications, into the system 100 (Step 1020). Once the patient's demographic information has been entered into the system 100, the patient reads and responds to each question on a corresponding questionnaire (Step 1025) and, subsequently, enters each response into the system 100, such as for comparison with responses that have been preprogramed into the system 100 associated with certain personality traits and disorders.

The micro-lab device 120 is then used to analyze samples of the patient's bodily fluids, such as blood B, urine U, and saliva S. Namely, each sample is put on a corresponding slide 510a-510c and each slide 510a-510 is then inserted into a corresponding slot 500a-500c of the micro-lab device 120, such that the bodily fluid can be scanned by the scanner 600 so as to determine the body chemistry of the patient (Step 1030).

Once all the data, such as from the facial recognition device 110, the demographic questions, each questionnaire, and from the micro-lab device 120, has been obtained, the data is entered into a software program 1035, which is referred to as "Go Falcon." The software program 1035 (i.e. "Go Falcon"), in turn, communicates with a database 1037, such as a cloud database containing available information relating to personality traits, illnesses, psychological factors, and physiological factors. For example, after all the data has been entered into the software program 1035 (i.e. "Go Falcon"), preprogrammed calculations in the software program 1035 (i.e. "Go Falcon") are utilized to match the patient's personality traits, illnesses, and other information with a suitable treatment stored in the database 1037 (e.g., treatments appropriate for a specific age, for example). Such a comparison can, in turn, be used to determine the appropriate treatment for the patient (Step 1040), such as by specifying factors, such as nutrition 1047, feelings 1049, diet 1051, such organic supplements (i.e. herbs), activities 1053, such as sports, and religion 1055, as well as music 1056, energy 1059, color 1061, and culture 1063. It is to be noted that environmental factors, such as temperature, soil, water, and air quality, can also be taken into account when determining the patient's required treatment. In addition to correlation matching between the patient and the information contained in the database 1037, the database 1037 can also be searched using particular keywords so as to research possible treatment for the patient's disorder and create a treatment plan. For example, potential treatments for anxiety include eating pomegranates, orange carrots, apples, honey, peanuts, as well as drinking alkaline ionic water and kukisha tea. Once the software program 1035 (i.e "Go Falcon") has compared the patient's data with the data contained on the database 1037 and diagnosed the patient's disorder (Step 1040), a treatment report is created (Step 1057) for the patient. After the treatment report has been created (Step 1057), the process ends (Step 1060).

Once the treatment has been administered, the process 1000 can be repeated after a certain amount of time, such as fifteen days, a maximum duration for psychology treatment, so as to determine if the treatment is working or whether the treatment has to be modified.

It is to be understood that the present invention is not limited to the embodiments described above, but encompasses any and all embodiments within the scope of the following claims.

We claim:

1. A personality assessment and treatment determination system for a patient, comprising:
   a facial recognition device configured for imaging the patient's face and for identifying facial patterns related to predetermined distinct psychological disorders, wherein the facial recognition device displays questions to the patient related to psychological state assessments of the patient selected from the predetermined distinct psychological disorders consisting of anxiety, depression, frustration, shyness, and combinations thereof, further wherein the facial recognition device displays demographic questions to the patient;
   a micro-lab device in communication with the facial recognition device, the micro-lab device including a body having three slots, each of the three of slots being adapted for receiving a slide containing a distinct biological sample from the patient, wherein the distinct biological samples from the patient consist of blood, urine, and saliva on a respective slide, and a scanner configured for scanning each of the samples and provide results of the patient's body chemistry including the levels of Acetylcholine, Acetylcholinesterase, Serotonin, Adrenaline, pH, and Glucose, wherein the micro-lab device includes a selector switch configured for selecting the slide to be analyzed; and
   means for determining at least one psychological disorder associated with the patient and a treatment plan for the at least one psychological disorder based on a combination of the image data of the patient's face generated by the facial recognition device, the answers to the psychological and demographic questions, and the results associated with the scanned biological samples generated by the micro-lab device, wherein the treatment plan includes selection of treatment criteria selected from the group consisting of nutrition, feelings, diet, activities, religion, music, energy, color, culture, and combinations thereof.

2. The personality assessment and treatment determination system according to claim 1, further comprising a case having an interior portion and an exterior portion.

3. The personality assessment and treatment determination system according to claim 2, wherein the case comprises a portfolio case.

4. The personality assessment and treatment determination system according to claim 2, wherein the interior portion comprises a plurality of compartments.

5. The personality assessment and treatment determination system according to claim 2, wherein the exterior portion comprises a plurality of compartments.

6. A method for developing a psychological treatment strategy for a patient, comprising the steps of:
   providing a personality assessment and treatment determination system, the system comprising:
      i) a facial recognition device configured for imaging the patient's face and for identifying facial patterns related to predetermined distinct psychological disorders, wherein the facial recognition device displays questions to the patient related to psychological state assessments of the patient selected from the predetermined distinct psychological disorders consisting of anxiety, depression, frustration, shyness, and combinations thereof, further wherein the facial recognition device displays demographic questions to the patient;
      ii) a micro-lab device in communication with the facial recognition device, the micro-lab device including a body having three slots, each of the three of slots being adapted for receiving a slide containing a distinct biological sample from the patient, wherein the distinct biological samples from the patient consist of blood, urine, and saliva on a respective slide, and a scanner configured for scanning each of the samples and provide results of the patient's body chemistry including the levels of Acetylcholine, Acetylcholinesterase, Serotonin, Adrenaline, pH, and Glucose, wherein the micro-lab device includes a selector switch configured for selecting the slide to be analyzed; and
      iii) means for determining at least one psychological disorder associated with the patient and a treatment plan for the at least one psychological disorder based on a combination of the image data of the patient's face generated by the facial recognition device, the answers to the psychological and demographic questions, and the results associated with the scanned biological samples generated by the micro-lab device, wherein the treatment plan includes selection of treatment criteria selected from the group consisting of nutrition, feelings, diet, activities, religion, music, energy, color, culture, and combinations thereof;
   imaging the face of a patient using the facial recognition device to provide facial feature data;
   presenting questions to the patient, the questions relating to psychological states selected from the group consisting of anxiety, depression, shyness, frustration, and combinations thereof;
   receiving data from the patient in response to the questions to provide questionnaire data;
   receiving samples of a bodily fluid from the patient in the micro-lab device to provide biological data, the samples being selected from the group consisting of a blood sample, a urine sample, a saliva sample, and combinations thereof;

comparing the patient's facial feature data, questionnaire data, and biological data with a pre-recorded data set associated with a particular disorder;

diagnosing the patient's disorder based on the comparison; and generating a treatment report for the disorder based on known treatments for the diagnosed disorder.

* * * * *